(12) United States Patent
Kim

(10) Patent No.: US 6,293,136 B1
(45) Date of Patent: Sep. 25, 2001

(54) MULTIPLE MODE OPERATED SURFACE ACOUSTIC WAVE SENSOR FOR TEMPERATURE COMPENSATION

(75) Inventor: Yoonkee Kim, Freehold, NJ (US)

(73) Assignee: The United States of America as represented by the Secretary of the Army, Washington, DC (US)

(*) Notice: Subject to any disclaimer, the term of this patent is extended or adjusted under 35 U.S.C. 154(b) by 0 days.

(21) Appl. No.: 09/383,796

(22) Filed: Aug. 26, 1999

(51) Int. Cl.[7] ............................ G01N 29/02; G01N 29/24
(52) U.S. Cl. ...................... 73/19.03; 73/24.03; 73/24.06; 73/31.06; 73/61.75; 73/61.79; 73/64.53; 310/313 B; 310/313 D
(58) Field of Search ................................ 73/19.03, 24.01, 73/24.03, 24.06, 31.06, 61.75, 61.79, 64.53; 310/313 R, 313 B, 313 A, 313 D

(56) References Cited

U.S. PATENT DOCUMENTS

| | | | |
|---|---|---|---|
| 4,691,714 | * | 9/1987 | Wong et al. ........................ 128/738 |
| 5,235,235 | * | 8/1993 | Martin et al. ...................... 310/313 D |
| 5,869,763 | | 2/1999 | Vig et al. . |
| 6,044,332 | * | 3/2000 | Korsah et al. ........................ 702/76 |
| 6,076,406 | * | 6/2000 | Blair et al. ............................ 73/590 |

* cited by examiner

Primary Examiner—Helen Kwok
Assistant Examiner—Rose M. Miller
(74) Attorney, Agent, or Firm—Michael Zelenka; George B. Tereschuk

(57) ABSTRACT

A surface acoustic wave device sensor configured so as to have at least two different modes of operation. An acoustic response is obtained from each of the different modes of operation. The different modes of operation are a combination of a temperature effect and a measurand effect. The measurand effect is caused by the absorption and/or adsorption of a substance into a selective coating on the piezoelectric substrate. The two different modes of operation are effected differently by the temperature effect and therefore can be used to effectively eliminate the temperature effect by simultaneously solving equations representative of the different modes of operation. The present invention eliminates the need to provide other relatively more complicated temperature compensating structure or to maintain the device at a predetermined constant temperature. The present invention can be used to detect different chemicals or substances.

22 Claims, 4 Drawing Sheets

MULTIPLE MODE OPERATED SURFACE ACOUSTIC WAVE SENSOR FOR TEMPERATURE COMPENSATION

GOVERNMENT INTEREST

The invention described herein may be manufactured, used, sold, imported, and licensed by or for the Government of the United States of America without the payment to me of any royalty thereon.

FIELD OF THE INVENTION

The invention relates generally to a detector or sensor for detecting a substance, and more particularly to a surface acoustic wave sensor that compensates for temperature variations.

BACKGROUND OF THE INVENTION

Surface acoustic wave sensors are often used to detect the presence of substances, such as chemicals. A surface acoustic wave or SAW device acting as a sensor provides a highly sensitive detection mechanism due to the high sensitivity to surface loading and the low noise, which results from their intrinsic high Q factor. Surface acoustic wave devices are fabricated using photolithographic techniques with comb-like interdigital transducers placed on a piezoelectric material. Surface acoustic wave devices may have either a delay line or a resonator configuration. The selectivity of a surface acoustic wave device sensor is generally determined by a selective coating placed on the piezoelectric material. The absorption and/or adsorption of the species to be measured into the selective coating causes mass loading, elastic, and viscoelastic effects on the device. The change of the acoustic property due to the absorption and/or adsorption of the species can be interpreted as a delay time shift for the delay line surface acoustic wave device or a frequency shift for the resonator surface acoustic wave device. However, the response of the surface acoustic wave sensor is also effected by environmental changes, such as temperature, pressure, stress, among others. These environmental changes degrade the response of the surface acoustic wave sensor. Temperature generally has the severest effect on the response, which may cause a misinterpretation. In the past, low temperature coefficient material has been selected to reduce the temperature effect. However, this has not always been successful because the selective coating used on the piezoelectric material may change the temperature characteristics of the material. Precision control of the temperature of the sensor has also been utilized, with temperature being controlled in the range of milidegrees. However, such precise temperature control is difficult, and temperature gradients between the sensor and a temperature sensor for the temperature control generally cannot be avoided. To separate the temperature effect from the measurand effect in surface acoustic wave sensors, the upper harmonic mode operation utilizing dispersion in the layered structures and the two device configuration with perpendicular direction as a convolver has been suggested. In bulk acoustic wave resonator sensors, the dual mode operation of a SC-cut quartz resonator was suggested for a temperature compensation. Temperature compensation in other devices is known. For example, in U.S. Pat. No. 4,535,638 entitled "Resonator Transducer System With Temperature Compensation" issuing to Eer-Nisse et al on Aug. 20, 1985. Therein disclosed is an apparatus including an oscillator such as a quartz crystal, which is caused to resonate by the oscillator at two frequencies. The vibratory element is selected so that the two frequencies both vary with variations in force applied to the element and with variations in temperature of the element. Another device is disclosed in U.S. Pat. No. 5,869,763 entitled "Method For Measuring Mass Change Using A Quartz Crystal Microbalance" issuing to Vig et al on Feb. 9, 1999, which is herein incorporated by reference. Therein disclosed is a quartz crystal resonator excited in two different modes at the same time such that the mass change and the temperature change can be measured independently. The change in mass can be calculated accurately, independent of temperature effects.

Accordingly, there is a need to provide for temperature compensation in a surface acoustic wave sensor for detecting the presence of a substance or chemical.

SUMMARY OF THE INVENTION

The present invention is directed to a surface acoustic wave sensor that is operated with a crystal cut and propagation direction that can be operated simultaneously with a combination of different modes such as a surface acoustic wave (SAW)(or Rayleigh wave) mode, leaky surface acoustic wave (LSAW) mode or pseudo surface acoustic wave (PSAW) mode, and harmonics modes, such as the upper odd harmonics, from a single device layout. Each of these different modes have different temperature coefficients. The intrinsic dual mode operation of a single surface acoustic wave device sensor is utilized to separate the temperature effect from the measurand effect. The multi-mode or two-mode response is represented by multiple equations which may be solved to separate the response due to the temperature changes from the response due to the measurand.

Accordingly, it is an object of the present invention to provide a surface acoustic wave device sensor that provides accurate analysis of the exposed substance independent of temperature.

It is an advantage of the present invention that the surface acoustic wave device compensates for temperature variations.

It is a feature of the present invention that the surface acoustic wave device sensor operates with a multi-mode.

These and other objects, advantages, and features will be readily apparent in view of the following detailed description.

DETAILED DESCRIPTION OF THE PREFERRED EMBODIMENTS

Figure 1:
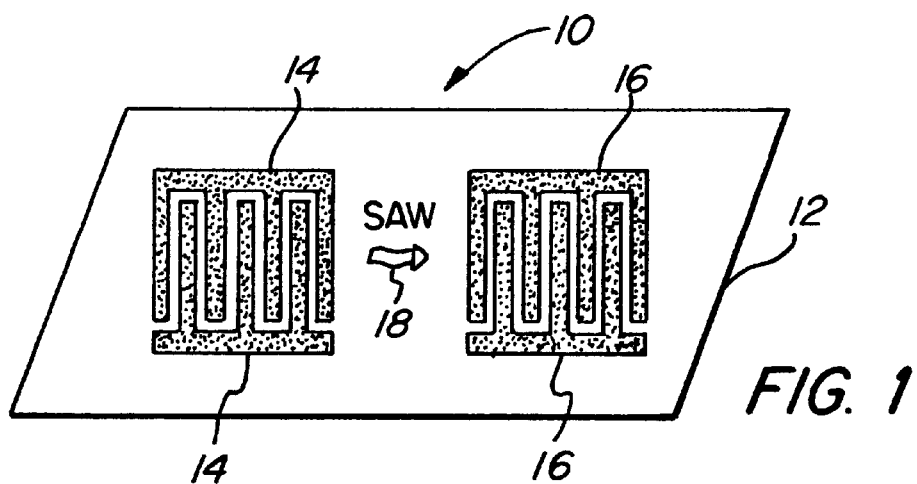
FIG. 1 is a plan view of a surface acoustic wave device sensor in a delay line configuration.

FIG. 1 is a plan view of a surface acoustic wave (SAW) device sensor 10 having a delay line configuration. The SAW device sensor 10 comprises a piezoelectric material 12 on which are placed input interdigital electrodes 14 and output interdigital electrodes 16. The interdigital electrodes 14 and 16 form transducers converting electrical energy into a surface acoustic wave. The surface acoustic wave is represented by arrow 18. Depending upon the crystal cut of the piezoelectric material and the propagation direction, a surface acoustic wave device can be operated simultaneously with the combination of a surface acoustical wave (SAW) (or Rayleigh wave), leaky surface acoustic wave (LSAW) or pseudo surface acoustic wave (PSAW), and harmonic modes from a single device layout or configuration. As an example, both surface acoustic waves and leaky surface acoustic waves exist in a thirty-six degree rotated Y-cut of lithium tantalate (LTO) with the free-surface acoustic velocities of 3125 meters per second and 4227 meters per second, respectively. Additionally, both surface acoustic wave (SAW) and leaky surface acoustic wave (LSAW) modes exist in a one hundred twenty-eight degree rotated Y-cut of lithium niobate (LNO) with velocities of 3580 meters per second and 4693 meters per second, respectively. There are many other possible selections of piezoelectric material, cut, and propagation directions that may be utilized in practicing the present invention. All of these may be determined without any undue experimentation. It is only necessary that the different modes have different temperature coefficients.

Figure 2A:
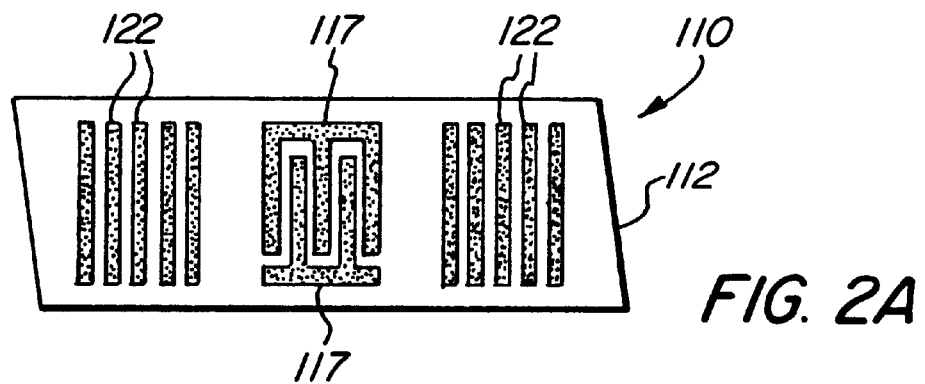
FIG. 2A is a plan view of a surface acoustic wave device sensor in a resonator configuration with a one-gate resonator.

FIG. 2A is a plan view of another sensor. A surface acoustic wave device sensor 110 has a resonator configuration with one gate. Formed on the piezoelectric material 112 are interdigital electrodes 117, acting as a transducer, and reflectors 122.

Figure 2B:
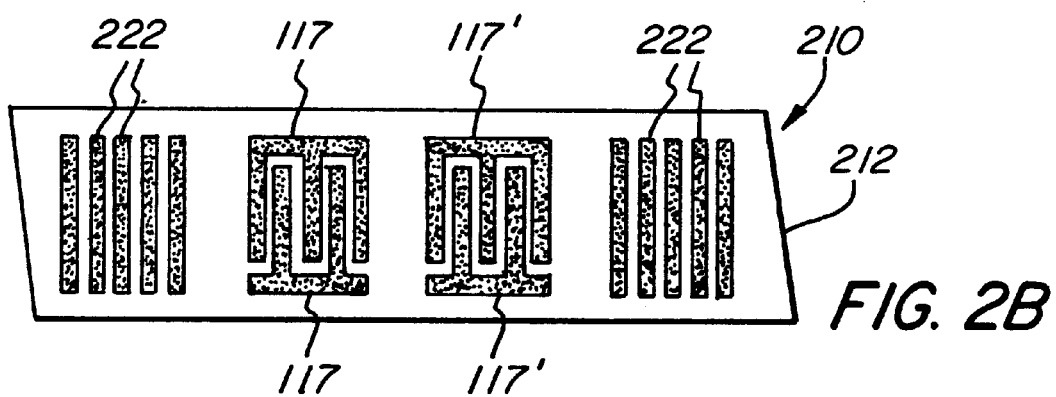
FIG. 2B is a surface acoustic wave device sensor in a resonator configuration having a two-gate resonator.

FIG. 2B illustrates another embodiment of a surface acoustic wave device sensor 210 having a resonator configuration with two gates. A piezoelectric material 212 has formed thereon two interdigital electrodes 117 and 117', acting as transducers. Bounding the two electrodes 117 and 117' are two reflectors 222.

Figure 3:
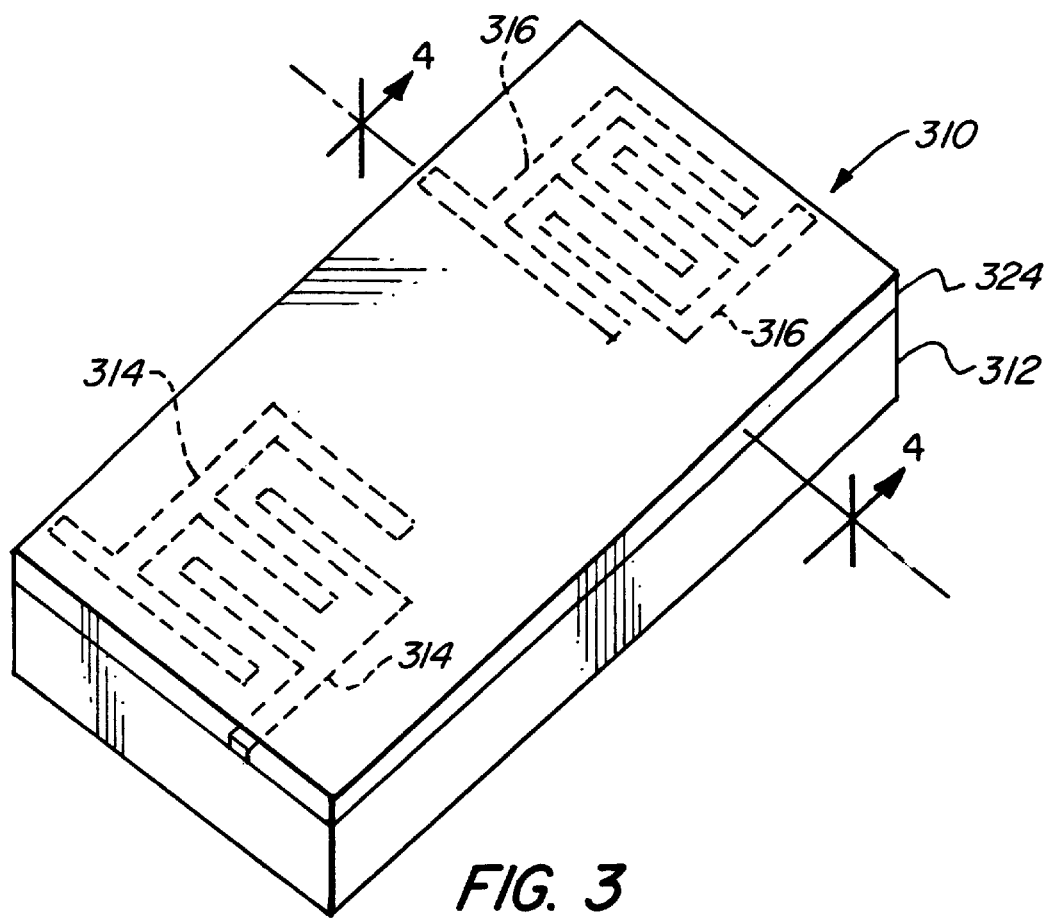
FIG. 3 is a perspective view of a surface acoustic wave device sensor.

FIG. 3 is a perspective view illustrating another embodiment of the present invention. A surface acoustic wave device sensor 310 has a delay line configuration. An input interdigital electrode 314 and an output interdigital electrode 316 are formed on and coupled to a piezoelectric substrate 312. The piezoelectric substrate 312 has a selective coating 324 thereon. The selective coating 324 is selected such that a particular species to be measured is absorbed by the selective coating 324 changing the acoustic properties of the surface acoustic wave device. Different selective coatings are well known. This change in acoustic properties is detected and is used to identify or detect the substance or species absorbed and/or adsorbed by the selective coating 324.

Figure 4:
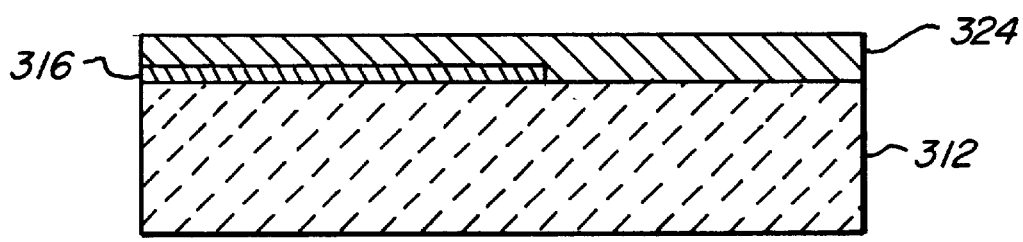
FIG. 4 is a cross section of the device illustrated in FIG. 3 taken along line 4—4.

FIG. 4 is a cross section taken along line 4—4 in FIG. 3. FIG. 4 more clearly illustrates the structure of the present invention. The selective coating 324 need not cover the entire planar surface of the piezoelectric substrate 312, but need only cover a portion thereof. The selective coating 324 illustrated covers the electrodes 314 and 316 and the entire planar surface of the piezoelectric substrate 312.

In operation, because the crystal cut and propagation direction of the surface acoustic wave device is selected to operate simultaneously in different modes, the intrinsic dual mode operation of a single surface acoustic wave device sensor may be utilized to separate the temperature effect from the measurand effect. The temperature effect is the change in acoustic property due to a change in temperature, and the measurand effect is the change in acoustic property due to the absorption and/or adsorption of the substance or material exposed to the selective coating. Accordingly, the multi-mode or two mode responses can be denoted by multiple or two simultaneous equations.

$$r_1 = f_1(m) + g_1(T)$$

$$r_2 = f_2(m) + g_2(T)$$

where,
  r represents the acoustic response with the subscripts referring to the mode, either surface acoustic wave or leaky surface acoustic wave or surface acoustic wave and their harmonic modes;
  f(m) represents the acoustic response function due to the measurand, material or substance being measured or detected, with the subscripts referring to the mode; and
  g(T) represents the acoustic response function due to the change in temperature, with the subscripts referring to the mode.

Of course, in the above, the acoustic response function f(m) is calibrated by obtaining the response of the selective coating to a measurand under a stabilized temperature condition. Additionally, the acoustic response function g(T) is calibrated for the temperature change effects without exposing it to a measurand; for example, in a vacuum or dry air. By simultaneously solving these two equations, the response due to the temperature changes can be separated from those due to the measurand effect. Therefore, the need to control temperature is unnecessary or made less strict. It is possible to utilize the teachings of the present invention to utilize the multi-mode operation in more than the two fundamental modes only. By utilizing more modes from higher harmonic modes, simultaneous equations may be solved to compensate for more effects, including other environmental effects, other than the temperature and measurand effects. For example higher order odd harmonic modes of the fundamental SAW mode may be used. Multiple harmonic modes may be used provided the different harmonic modes have a different response to an environmentally effect, such as temperature or pressure. Additionally, the present invention may be utilized in an array of sensors that have multiple coatings which may be utilized to increase the selectivity by a pattern recognition technique for chemical sensor applications. For example, an array of surface acoustic wave device sensors may be fabricated on a planar surface with selective coatings associated with each separate surface acoustic wave device in the array.

Figure 5:
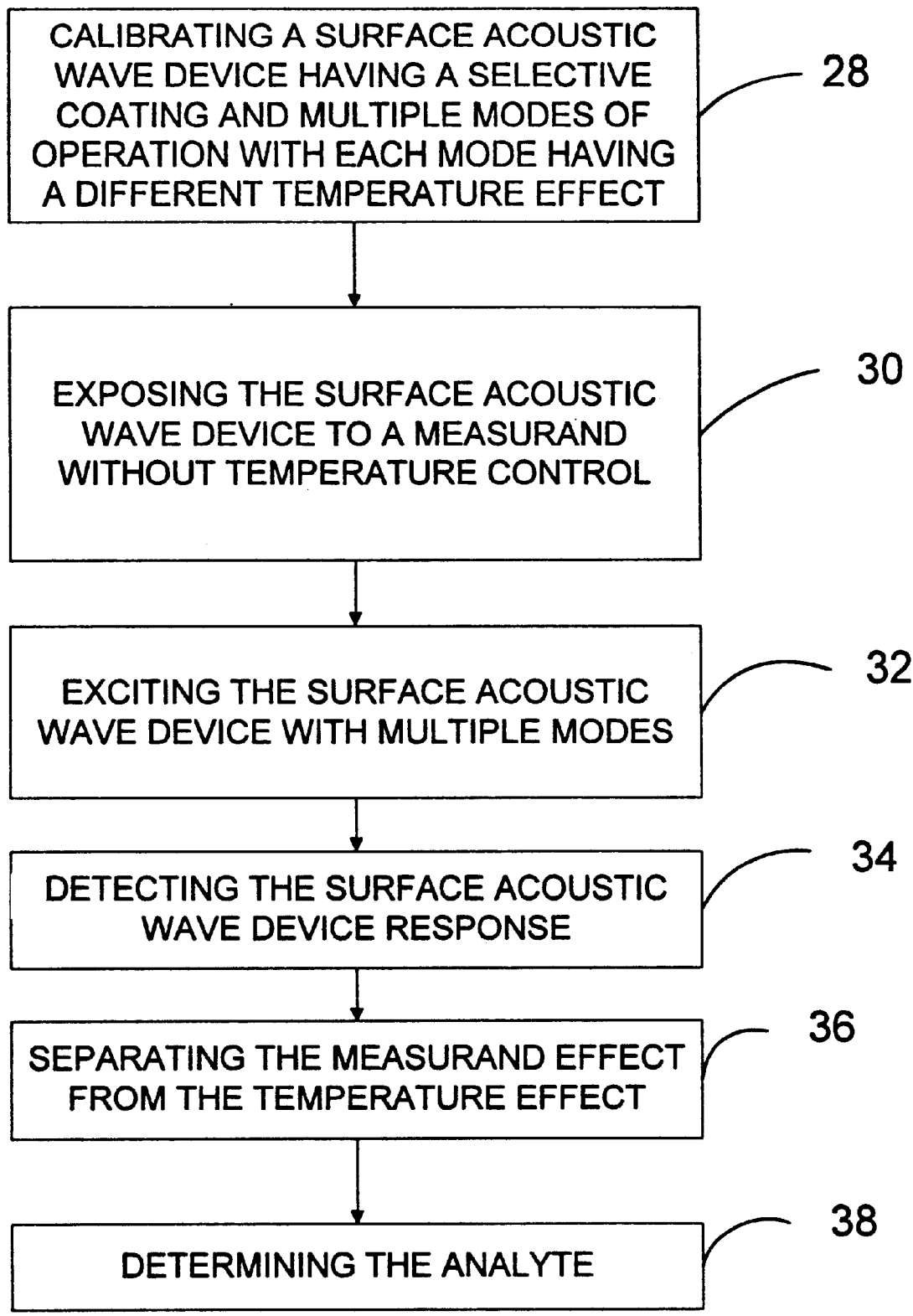
FIG. 5 is a block diagram illustrating the method steps of the present invention.

FIG. 5 is a block diagram illustrating the method steps of the present invention. Block 28 represents the initial calibration of the surface acoustic wave device with a selective coating for an environmental effect, such as temperature, and the measurand effect. Block 30 represents the step of exposing the surface acoustic wave device having a multi-mode of operation to an analyte or substance to be determined, with each mode having a different response to an environmental effect, such as a temperature effect, and a measurand effect or effect due to absorption and/or adsorption of a substance to be detected. Block 32 represents the step of exciting the surface acoustic wave device such that a surface acoustic wave is transmitted through a selective coating resulting in a modified acoustic property due to the absorption and/or adsorption of the analyte or substance. Block 34 represents the step of detecting the surface acoustic wave device response. Block 36 represents the step of separating the measurand effect from the temperature effect. This step effectively represents the simultaneous solution of the two equations to solve for the measurand effect, effectively eliminating the temperature effect. Block 38 represents the step of determining the analyte. This step is achieved by detecting the changed acoustic properties of the selective coating with a substance absorbed therein. Based upon the change in acoustic properties, the analyte can be determined by known techniques.

Figure 6:
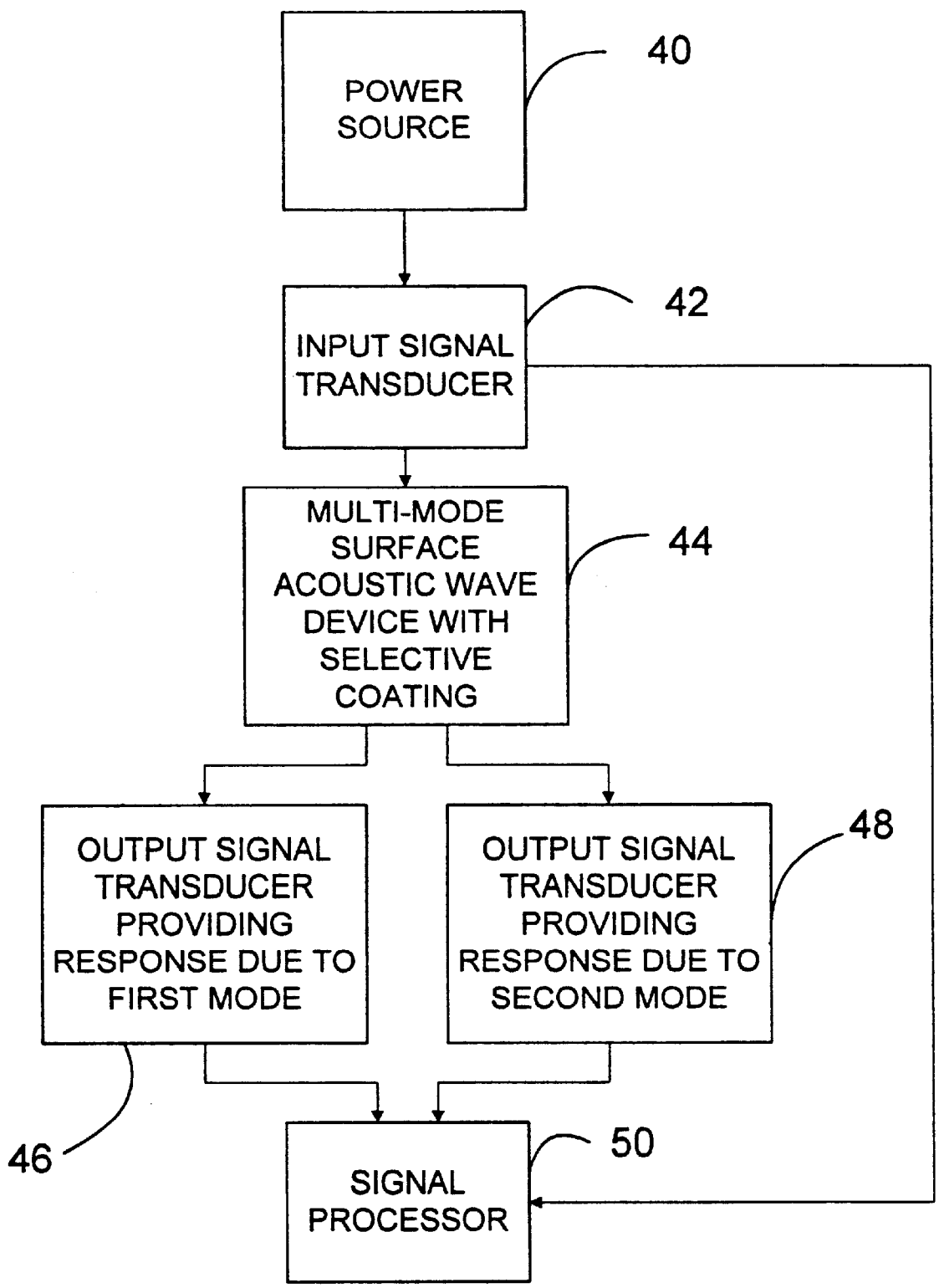
FIG. 6 is a schematic diagram illustrating the present invention.

FIG. 6 is a schematic illustration of the present invention. A power source 40 provides power to drive an input signal transducer 42. The input signal transducer 42 is coupled to a multi-mode surface acoustic wave device 44. The multi-mode surface acoustic wave device 44 has a selective coating thereon. An output signal transducer 46 is coupled to the multi-mode surface acoustic wave device 44 and provides a response due to a first mode. An output signal transducer 48 is coupled to the multi-mode surface acoustic wave device 44 and provides a response due to a second mode. The input signal transducer 42 and output signal transducers 46 and 48 are coupled to a signal processor 50. The signal processor 50 determines any delay time shift, in a delay line surface acoustic wave device, or a frequency shift, in a resonator surface acoustic wave device. This change in acoustic properties results in detection and characterization of the analyte, material, or substance absorbed in the selective coating. By obtaining an output signal from multiple modes of operation, different environmental effects, such as temperature, can be effectively eliminated.

Accordingly, it should be appreciated that the present invention, in providing a surface acoustic wave device sensor that can effectively determine or detect an analyte or substance substantially independent of temperature, makes possible the use of the present invention in many different applications. The need to control temperature is greatly reduced. This eliminates the need for other more complicated structures that have been utilized to compensate for temperature coefficients or their effect on a sensor. The concept of the present invention in utilizing different modes in a surface acoustic wave device sensor may be applied to effectively eliminate other effects that may interfere with the measurand effect, such as different environmental effects other than temperature.

Although the preferred embodiment has been illustrated and described, it will be obvious to those skilled in the art that various modifications may be made without departing from the spirit and scope of this invention.

What is claimed is:

1. A surface acoustic wave device sensor, comprising:
    a piezoelectric material, said piezoelectric material capable of propagating a surface acoustic wave in a first mode and a second mode;
    a selective coating having acoustic properties placed on said piezoelectric material, whereby an analyte exposed to said selective coating alters the acoustic properties of said selective coating;
    an input interdigital transducer and an output interdigital transducer are coupled to said piezoelectric material, whereby said input interdigital transducer generates a surface acoustic wave in the first and second mode on said selective coating of the piezoelectric material, said output interdigital transducer receiving said surface acoustic wave;
    a signal processor coupled to said transducer, said signal processor receiving signals representative of the surface acoustic wave propagated in the first and second mode and the acoustic properties of said selective coating, said signal processor separating a measurand effect from an environmental effect,
    whereby the analyte is detected due to a change in the acoustic properties of said selective coating;
    the first mode is a surface acoustic wave mode; and
    the second mode is a leaky surface acoustic wave mode.

2. A surface acoustic wave device sensor, as recited in claim 1, further comprising said piezoelectric material is lithium tantalate.

3. A surface acoustic wave device sensor, as recited in claim 2, wherein:
    said piezoelectric material is y-cut.

4. A surface acoustic wave device sensor, as recited in claim 2, wherein:
    said piezoelectric material is rotated.

5. A surface acoustic wave device sensor, as recited in claim 4, wherein:
    said piezoelectric material is 36° rotated y-cut.

6. A surface acoustic wave device sensor, as recited in claim 1, further comprising said piezoelectric material is lithium niobate.

7. A surface acoustic wave device sensor, as recited in claim 6, wherein:
    said piezoelectric material is y-cut.

8. A surface acoustic wave device sensor, as recited in claim 7, wherein:
    said piezoelectric material is rotated.

9. A surface acoustic wave device sensor, as recited in claim 8, wherein:
    said piezoelectric material is 128° rotated y-cut.

10. The surface acoustic wave device sensor, as recited in claim 1, further comprising said output interdigital transducer placed on said piezoelectric material forms a delay line.

11. The surface acoustic wave device sensor, as recited in claim 1, further comprising a first reflector placed on said piezoelectric material adjacent to said input interdigital transducer forms a resonator.

12. The surface acoustic wave device sensor, as recited in claim 11, further comprising a second reflector is placed on said piezoelectric material between said first reflector and said second reflector.

13. A surface acoustic wave device sensor having a delay line configuration used to detect a substance, comprising:
    a piezoelectric material, said piezoelectric material propagating a surface acoustic wave in a first mode and a second mode;
    a selective coating having acoustic properties placed on said piezoelectric material, whereby a substance exposed to said selective coating alters the acoustic properties of said selective coating;
    an input signal transducer formed on said piezoelectric material causing said piezoelectric material to propagate the surface acoustic wave in the first and second modes;
    an output signal transducer formed on said piezoelectric material separated from said input signal transducer and having at least a portion of said selective coating between said input signal transducer and said output signal transducer, whereby the first and second modes are propagated through said selective coating; and
    a signal processor coupled to said input signal transducer and said output signal transducer calculates a delay time shift;
    said signal processor calculating a measurand effect based upon the first and second modes,
    whereby said measurand effect is separated from a temperature effect to provide temperature compensation and to permit detecting a plurality of changes in the acoustic properties of said selective coating of the substance despite environmental effects and independent of said temperature effect.

14. A surface acoustic wave device sensor having a resonator configuration used to detect a substance, comprising:

a piezoelectric material, said piezoelectric material capable of propagating a surface acoustic wave in a first mode and a second mode;

a selective coating having acoustic properties placed on said piezoelectric material, whereby a substance exposed to said selective coating alters the acoustic properties of said selective coating;

a signal transducer formed on said piezoelectric material causing said piezoelectric material to propagate the surface acoustic wave in the first and second modes;

a first reflector formed on said piezoelectric material separated from said signal transducer and having at least a portion of said selective coating between said signal transducer and said first reflector, whereby the first and second modes are propagated through said selective coating;

said signal transducer transmits the surface acoustic wave in the first and second modes to a signal processor; and said signal processor is coupled to said signal transducer, said signal transducer receives the surface acoustic wave in first and second modes, said signal processor calculating a measurand effect based upon the first and second modes, said measurand effect being separated from a temperature effect to provide temperature compensation, whereby changes in the acoustic properties of said selective coating caused by the substance are detected independent of said temperature effect.

15. A surface acoustic wave devise sensor having a resonator configuration, as recited in claim 14, further comprising:

a second reflector formed on said piezoelectric material so that said signal transducer is positioned between said first and second reflectors.

16. A surface acoustic wave device sensor, comprising:

a piezoelectric material capable of simultaneously operating in at least two different modes, with each mode having a different response to an environmental effect;

a selective coating placed on said piezoelectric material, whereby when a substance is placed in contact with said selective coating the acoustic properties of said selective coating are changed;

means, coupled to said selective coating, for detecting the acoustic properties of the selective coating based upon a response of each of the two different modes; and means, coupled to said means for detecting, for identifying the substance placed in contact with said selective coating, whereby environmental effects, including a temperature effect are effectively removed due to the different responses of the at least two different modes and separating a measurand effect from said temperature effect provides temperature compensation to detect the changes in the acoustic properties caused by the substance independent of said temperature effect.

17. A method of detecting a substance with a surface acoustic wave device sensor having a selective coating, comprising the steps of:

exciting the surface acoustic wave device in a first mode;

exciting the surface acoustic wave device in a second mode, said second mode having a different response due to a plurality of environmental effects differing from that of the first mode, said environmental effects including a temperature effect;

determining the initial acoustic properties of the surface acoustic wave device;

exposing the selective coating to a substance;

separating a temperature effect from a measurand effect to provide temperature compensation;

determining the resulting acoustic properties of the surface acoustic wave device resulting from said exposing step and said separating step; and identifying the substance based upon the resulting acoustic properties independent of said temperature effect.

18. A method of detecting a substance, as recited in claim 17, wherein:

the environmental effect is temperature.

19. A method of detecting a substance, as recited in claim 17, wherein:

the second mode is a harmonic of the first mode.

20. A method of detecting a substance, as recited in claim 17, wherein:

the second mode is a harmonic of another mode.

21. A method of detecting a substance with a surface acoustic wave device having a selective coating and multiple modes, comprising the steps of:

calibrating the surface acoustic wave device for a plurality of temperature effects and a measurand effect;

exposing said selective coating of the surface acoustic wave device to the substance;

exciting the surface acoustic wave device with multiple modes, with each mode having a different response to one of the plurality of temperature effects;

detecting the surface acoustic wave response for each mode;

separating the measurand effect from each of the plurality of temperature effects; and determining the substance based upon the measurand effect independent of said plurality of temperature effects.

22. A method of detecting a substance, as recited in claim 21, further comprising a plurality of environmental effects is equal to the number of modes.

* * * * *